United States Patent
Ning et al.

(10) Patent No.: US 10,624,379 B2
(45) Date of Patent: Apr. 21, 2020

(54) COMPOSITION, METHOD FOR PRODUCING THE SAME AND USE THEREOF

(71) Applicant: INFINITUS (CHINA) COMPANY LTD., Jiangmen, Guangdong (CN)

(72) Inventors: Deshan Ning, Guangdong (CN); Hongwei Zhao, Guangdong (CN); Qingtao Tang, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

(21) Appl. No.: 16/217,045

(22) Filed: Dec. 12, 2018

(65) Prior Publication Data

US 2019/0373936 A1    Dec. 12, 2019

(30) Foreign Application Priority Data

Jun. 7, 2018   (CN) .......................... 2018 1 0581270

(51) Int. Cl.

| | |
|---|---|
| *A61K 36/00* | (2006.01) |
| *A23L 33/105* | (2016.01) |
| *A23L 33/21* | (2016.01) |
| *A61K 36/734* | (2006.01) |
| *A61K 36/736* | (2006.01) |
| *A61K 36/355* | (2006.01) |
| *A61K 31/733* | (2006.01) |
| *A61K 47/36* | (2006.01) |
| *A61K 47/26* | (2006.01) |
| *A61K 47/12* | (2006.01) |
| *A61P 3/06* | (2006.01) |
| *A23L 33/125* | (2016.01) |

(52) U.S. Cl.
CPC ........... *A23L 33/105* (2016.08); *A23L 33/125* (2016.08); *A23L 33/21* (2016.08); *A61K 31/733* (2013.01); *A61K 36/355* (2013.01); *A61K 36/734* (2013.01); *A61K 36/736* (2013.01); *A61K 47/12* (2013.01); *A61K 47/26* (2013.01); *A61K 47/36* (2013.01); *A61P 3/06* (2018.01); *A23V 2002/00* (2013.01); *A23V 2200/30* (2013.01); *A23V 2250/032* (2013.01); *A23V 2250/21* (2013.01); *A23V 2250/262* (2013.01); *A23V 2250/5062* (2013.01); *A23V 2250/5072* (2013.01); *A23V 2250/6422* (2013.01); *A23V 2300/10* (2013.01); *A23V 2300/14* (2013.01); *A23V 2300/31* (2013.01); *A23V 2300/48* (2013.01); *A23V 2300/50* (2013.01); *A61K 2236/15* (2013.01); *A61K 2236/31* (2013.01); *A61K 2236/331* (2013.01); *A61K 2236/51* (2013.01)

(58) Field of Classification Search
None
See application file for complete search history.

(56) References Cited

FOREIGN PATENT DOCUMENTS

CN    101623089 A  *  1/2010

OTHER PUBLICATIONS

Zeng Xiao-yu, Recent advance and future trend of Inulin research and development, China food additives, Aug. 15, 2010, pp. 224.
Wang Dai-ming, Experimental study on the effect of hawthorn extract on regulating blood lipid, Clinical Journal of traditional Chinese Medicine, CJTCM Dec. 20, 2012, vol. 24 No. 12, pp. 1147-1148.
Wang-Qiang, Effect of honeysuckle extract on blood lipid and blood glucose, Pharmacology and Clinics of Chinese Materia Medica, Jun. 15, 2007, 23(3), pp. 40-42.

* cited by examiner

*Primary Examiner* — Qiuwen Mi
(74) *Attorney, Agent, or Firm* — Yue Robert Xu; Apex Attorneys at Law, LLP

(57) ABSTRACT

The present disclosure relates to the field of healthcare products. Disclosed is a composition comprising inulin, concentrated hawthorn juice, honeysuckle extract and concentrated peach juice, which is without adding flavor, pigment, preservative, sucrose and honey, also without adding animal-sourced raw materials, and allergens such as gluten, beans and so on. In addition, dosage required for the composition is small; it is easy to be taken and can be dissolved in water. The method for producing the composition in the present disclosure is simple and suitable for large-scale production. The composition obtained has a good stability and long storage time. Experiments show that the composition provided by the present disclosure has a function of facilitating lowering triglyceride, and the effect is significant. The composition can be used in manufacture of healthcare foods having a function of lowering blood lipid and improving digestion.

4 Claims, 6 Drawing Sheets

COMPOSITION, METHOD FOR PRODUCING THE SAME AND USE THEREOF

CROSS REFERENCE TO RELATED APPLICATIONS

This application claims the priority of Chinese Patent Application No. 201810581270.4, filed on Jun. 7, 2018, and the disclosures of which are hereby incorporated by reference.

FIELD

The present disclosure relates to the field of healthcare products and foods, specifically to a composition, method for producing the same and use thereof.

BACKGROUND

With continuous improvement of the living standards of people, the development of urbanization and industrialization, people's eating habits have been changed, and physical activities has gradually decreased. Hyperlipidemia becomes a serious risk to human health. Hyperlipidemia is a common disease caused by abnormal lipid metabolism in the body. It mainly refers to unduly high levels of total cholesterol, triglyceride and low-density lipoprotein in serum or unduly low low-density lipoprotein level in serum. There is no obvious clinical symptom in the early stage of hyperlipidemia, and its damage to the body is nonobvious, progressive and systemic. Hyperlipidemia may accelerate atherosclerosis, and the blockage of artery will cause many diseases, such as cardiovascular and cerebrovascular diseases, kidney disease, liver disease and so on. Cardiovascular and cerebrovascular diseases are the leading cause of death in the middle-aged and elderly people and are the number one killer that threatens human health. According to the World Health Organization, about 17 million people die from this chronic disease each year, accounting for about 30% of the total global death toll. In other words, one out of every three dead people is caused by cardiovascular disease.

Modern medical studies have shown that the factors affecting human blood lipid levels mainly include genetic factors and environmental factors. However, the influence of genetic factors is limited, and blood lipid level is mainly affected by environmental factors. The environmental factors that affect human blood lipid level are as follows: (1) High cholesterol and high saturated fatty acid diet. Studies have shown that when the body takes in a lot of saturated fatty acids and high cholesterol, the cholesterol and triglyceride content in the blood will be too high, forming hyperlipidemia. (2) High-starch diet. Results of some studies suggest that when the proportion of taking-in sugar is too high, the blood glucose rises, stimulating insulin secretion, and causing hyperinsulinemia. The latter increases the synthesis of triglyceride and very low-density pre-β-lipoprotein, causing hyperlipidemia. (3) Obesity. Obesity promotes liver exporting apolipoprotein B-contained lipoproteins, which increases the generation of low-density lipoprotein and more likely cause hyperlipidemia. (4) Lack of exercise. People who are sedentary have higher plasma triglyceride concentrations than those who keep physical exercise.

Current studies have shown that the object of lowering blood lipid can be achieved by inhibiting the absorption and synthesis of lipids, or promoting the decomposition and excretion of lipids. Polyunsaturated fatty acids, including fish oil, seal oil, various vegetable oils and so on, can facilitate lowering blood lipid mainly through inhibiting the synthesis of endogenous cholesterol and triglycerides, increasing the activity of lipoprotein lipase, promoting the clearance of very low-density lipoproteins in surrounding tissues, lowering the content of triglycerides, cholesterol and low-density lipoprotein in serum, and increasing the content of high-density lipoprotein.

With the development of economy and science, people's requirements for quality of life are getting higher and higher, and they gradually realize the importance of "preventing problems before they happen" and pay more attention to health than ever before. Research on drugs and healthcare foods is a common concern of the society. The development of healthcare foods having a function of facilitating lowering blood lipid has huge market demand, broad prospects and important practical significance.

SUMMARY

In view of above, the present disclosure provides a composition, method for producing the same and use thereof. The composition has a function of facilitating lowering triglyceride, and the effect is significant. The composition can be used in preparing healthcare foods having a function of lowering blood lipid and improving digestion.

In order to achieve the above goals, the following technical solutions are provided by the present disclosure.

The present disclosure provides a composition, comprising inulin, concentrated hawthorn juice, honeysuckle extract and concentrated peach juice In some embodiments of the present disclosure, the mass ratio of inulin, the concentrated hawthorn juice (with a solid content of 40~70%), the honeysuckle extract and the concentrated peach juice (with a solid content of 40~70%) is (1200~2400):(1200~2400):(50~200):(20~100).

In some embodiments of the present disclosure, the composition further comprises one selected from the group consisting of pectin, xylitol, stevioside, citric acid, and mogroside, or a mixture thereof.

In some embodiments of the present disclosure, the mass ratio of inulin, the concentrated hawthorn juice (with a solid content of 40~70%), honeysuckle extract, the concentrated peach juice (with a solid content of 40~70%), pectin, xylitol, stevioside, citric acid and mogroside is (1200~2400):(1200~2400):(50~200):(20~100):(30~50):(25~50):(10~50):(10~50):(5~15).

In some embodiments of the present disclosure, the mass ratio of inulin, the concentrated hawthorn juice (with a solid content of 60%), honeysuckle extract, the concentrated peach juice (with a solid content of 60%), pectin, xylitol, stevioside, citric acid and mogroside in the composition is 1600:1800:110:40:45:35:30:15:6.

The present disclosure further provides a method for producing the composition, comprising:

Step 1: juicing fresh hawthorn fruits, collecting filtrate upon filtration, and concentrating to obtain a concentrated hawthorn juice with a solid content of 40~70%; adding water 1~3 times (w/w) of the concentrated hawthorn juice, dissolving at 80~90° C., and subjecting the resultant to UHT sterilization to obtain a first solution for use; taking 60~90% (w/w) formula amount of inulin, adding water 3~6 times (w/w) of the inulin, dissolving at 80~90° C., and subjecting the resultant to UHT sterilization to obtain a second solution for use; mixing the first solution with the second solution, performing freeze-drying, and pulverizing the resulting freeze-dried powders with a 40~200 meshes sieve to obtain hawthorn powders;

Step 2: juicing fresh peach fruits, collecting filtrate upon filtration, and concentrating to obtain a concentrated peach juice with a solid content of 40~70%; adding water 1~3 times (w/w) of the concentrated peach juice, dissolving at 80~90° C., and subjecting the resultant to UHT sterilization to obtain a third solution for use; taking the rest amount of inulin, adding water 3~6 times (w/w) of the inulin, dissolving at 80~90° C., and subjecting the resultant to UHT sterilization to obtain a fourth solution for use; mixing the third solution with the fourth solution, performing freeze-drying, and pulverizing the resulting freeze-dried powders with a 40~200 meshes sieve to obtain peach powders;

Step 3: mixing honeysuckle with water and performing extraction, collecting filtrate upon filtration, concentrating, drying and pulverizing with a 40~200 meshes sieve to obtain the honeysuckle extract;

Step 4: mixing the hawthorn powders obtained in Step 1, the peach powders obtained in Step 2 and the honeysuckle extract obtained in Step 3 to obtain the composition; and wherein, there is no restriction on the order of Step 1, Step 2 and Step 3.

In some embodiments of the present disclosure, the method comprises the following steps:

Step 1: juicing fresh hawthorn fruits, collecting filtrate upon filtration, and concentrating to obtain a concentrated hawthorn juice with a solid content of 40~70%; adding water 1~3 times (w/w) of the concentrated hawthorn juice, dissolving at 80~90° C., and subjecting the resultant to UHT sterilization to obtain a first solution for use; taking 60~90% (w/w) formula amount of inulin, adding water 3~6 times (w/w) of the inulin, dissolving at 80~90° C., and subjecting the resultant to UHT sterilization to obtain a second solution for use; mixing the first solution with the second solution, performing freeze-drying, and pulverizing the resulting freeze-dried powders with a 40~200 meshes sieve to obtain hawthorn powders;

Step 2: juicing fresh peach fruits, collecting filtrate upon filtration, and concentrating to obtain a concentrated peach juice with a solid content of 40~70%; adding water 1~3 times (w/w) of the concentrated peach juice, dissolving at 80~90° C., and subjecting the resultant to UHT sterilization to obtain a third solution for use; taking the rest amount of inulin, adding water 3~6 times (w/w) of the inulin, dissolving at 80~90° C., and subjecting the resultant to UHT sterilization to obtain a fourth solution for use; mixing the third solution with the fourth solution, performing freeze-drying, and pulverizing the resulting freeze-dried powders with a 40~200 meshes sieve to obtain peach powders;

Step 3: mixing honeysuckle with water and performing extraction, collecting filtrate upon filtration, concentrating, drying and pulverizing with a 40~200 meshes sieve to obtain the honeysuckle extract;

Step 4: mixing the hawthorn powders obtained in Step 1, the peach powders obtained in Step 2 and the honeysuckle extract obtained in Step 3, and the other ingredients according to formula to obtain the composition; and wherein, there is no restriction on the order of Step 1, Step 2 and Step 3.

In some embodiments of the present disclosure, the concentrating in Step 1 and Step 2 is a vacuum concentration or a reverse osmosis concentration;

the extraction in Step 3 is a decoction extraction, a low-temperature high-speed counter-current extraction or an ultrasonic extraction; the decoction extraction comprises two extractions, the first extraction is performed by adding water 12~25 times (w/w) of the starting material and extracting for 40~120 min, and the second extraction is performed by adding water 10~13 times (w/w) of the starting material and extracting for 10~120 min; the low-temperature high-speed counter-current extraction is performed by adding water 12~25 times (w/w) of the starting material and extracting at 40~60° C. for 40~120 min; and the ultrasonic extraction is performed by adding water 12~25 times (w/w) of the starting material and extracting at 40~60° C. for 40~120 min, and the ultrasonic frequency is 20~50 kHZ; and the drying in Step 3 is selected from the group consisting of spray drying, freeze drying, belt drying, microwave drying and vacuum drying.

In some embodiments of the present disclosure, the extraction in Step 3 is a decoction extraction; and the decoction extraction comprises two extractions, the first extraction is performed by adding water 8~15 times (w/w) of the starting material and extracting for 60~100 min, and the second extraction is performed by adding water 6~12 times (w/w) of the starting material and extracting for 40~80 min.

Use of the composition provided by the present disclosure or the composition produced by the method provided by the present disclosure in manufacture of healthcare foods and/or drugs having a function of lowering triglyceride.

The present disclosure provides a composition comprising inulin, concentrated hawthorn juice, honeysuckle extract and concentrated peach juice, which is without adding flavor, pigment, preservative, sucrose and honey, also without adding animal-sourced raw materials, and allergens such as gluten, beans and so on, therefore in line with people's pursuit of natural and health foods. In addition, dosage required for the composition is small; it is easy to be taken and can be dissolved in water; it is soluble in cold water and can be absorbed quickly. The method for producing the composition in the present disclosure is simple and suitable for large-scale production. Also, it is easy to be carried. The composition obtained has a good stability and long storage time. Experiments show that the composition provided by the present disclosure has a function of facilitating lowering triglyceride, and the effect is significant. The composition can be used in manufacture of healthcare foods having a function of lowering blood lipid and improving digestion.

BRIEF DESCRIPTION OF DRAWINGS

In order to illustrate the technical solutions in the examples of the present disclosure or the conventional arts more clearly, the drawings used for illustrating the examples or conventional art will be described briefly hereinafter.

DETAILED DESCRIPTION

Figure 1:
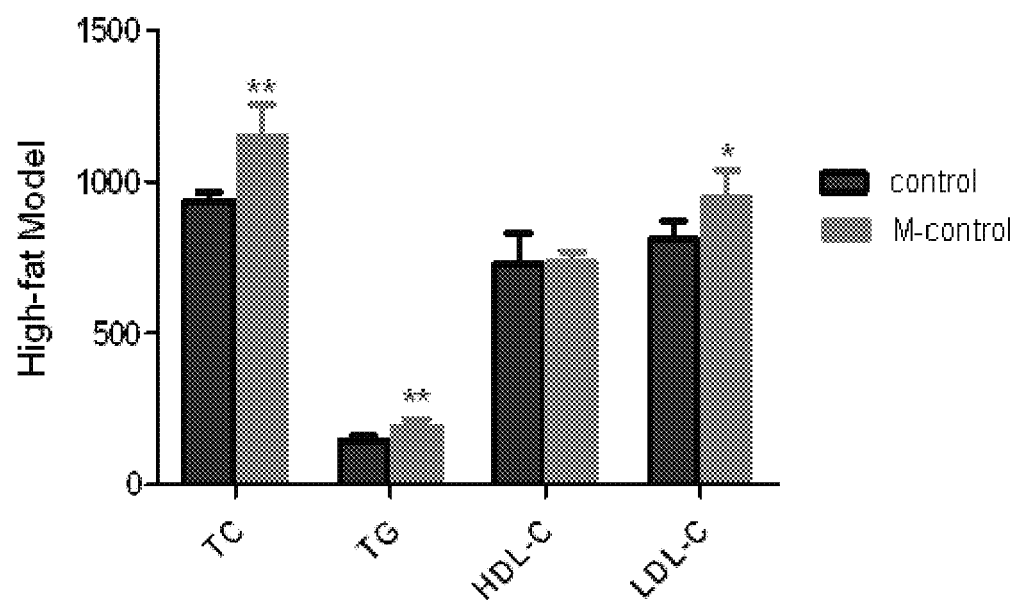
FIG. 1 shows TG, TC, HDL-C and LDL-C contents in the serum of the blank group and model group of SD rats; and * indicates comparing the model group with the blank group, * indicates P<0.05, and ** indicates P<0.01.

The present disclosure provides a composition, a method for producing the same and the use thereof. One of ordinary skill in the art can learn from the contents of this document and appropriately improve the process parameters. It is to be understood that all such alternatives and modifications are obvious to one of ordinary skill in the art and are considered to be included in the present disclosure. The methods and applications of the present disclosure have been described in terms of preferred embodiments. It will be apparent to one of ordinary skill in the art that the methods and applications described herein may be modified or modified and combined to implement and practice the techniques of the present disclosure without departing from the scope of the present disclosure.

In the present disclosure, reference was made to the method for testing the function of facilitating lowering blood-lipid in the *Technical specification for health care food inspection and evaluation* (2012 *Updated Edition*). SPF grade male SD rats were used as experimental animals. After the adaption period, an animal model of the combined hyperlipidemia was established, and the rats were randomly divided into groups according to TC level. Three dosage groups were continuously administered with the composition provided by the present disclosure by gavage at a dosage of 500 mg/kg·BW (equaled to 5 times of recommendation amount for human), 1000 mg/kg·BW (equaled to 10 times of recommendation amount for human) and 2500 mg/kg·BW (equaled to 25 times of recommendation amount for human), respectively. The blank control group and the model control group were administered with the same volume of distilled water by gavage. Each group was weighed regularly. 30 days after the administration, blood samples were collected without fasting, and levels of TC, TG, HDL-C, LDL-C, ox-HDL, ox-LDL, apo-A1 and apo-β were tested.

The results are shown hereinafter.

(1) In the animal experiments, when comparing the model control group with the blank control group, TG content in serum increased, TC and LDL-C content in serum increased, and the differences were significant, which indicated that the combined hyperlipidemia SD rat model was successfully established.

(2) The weight growth of each dosage group and the model control group, which were fed with high-fat diet, were significantly higher than that of the blank control group fed with maintenance diet. But there was no significant difference between each dosage group and the model control group. Results of the present experiments showed that the composition provided by the present disclosure did not have an obvious effect on weight of SD rat.

(3) The total cholesterol (TC) contents of the high, middle and low dosage groups of the composition provided by the present disclosure were respectively 1168.54 μmol/L, 1159.86 μmol/L and 1184.54 μmol/L. Comparing with the model control group (1148.96 μmol/L), there was no significantly difference after a statistical analysis (P>0.05). Results of the present experiment showed that the composition provided by the present disclosure did not have an obvious effect on TC content in serum of SD rat.

(4) Triglyceride (TG) content in serum of the high dosage group of the composition provided by the present disclosure was 154.9 μmol/L, and there was a significant difference (P=0.040, <0.05) comparing with the model control group (190.62 μmol/L). TG contents in serum of the middle and low dosage groups were respectively 195.92 μmol/and 208.59 μmol/L, and there was no significant difference (P were respectively 0.751 and 0.352, and >0.05) comparing with the model control group. Results of the present experiment showed that high dosage group of the composition provided by the present disclosure significantly decreased the TG content in serum of SD rat.

(5) HDL-C content of high dosage group of the composition provided by the present disclosure was 849.23 μmol/L, and there was a significant difference (P=0.039, <0.05) comparing with the model control group (734.66 μmol/L). HDL-C content of middle dosage group was 853.90 μmol/L, and there was no significant difference (P=0.275, >0.05) comparing with the model control group. HDL-C content of low dosage group was 861.74 μmol/L, and there was no significant difference (P=0.254, >0.05) comparing with the model control group. Results of the present disclosure showed that the high dosage group of the composition provided by the present disclosure significantly increased HDL-C content in serum of SD rat.

(6) LDL-C contents in serum of the high, middle and low dosage groups of composition provided by the present disclosure were respectively 870.88 μmol/L, 943.29 μmol/L and 941.32 μmol/L. Comparing with the model control group (947.36 μmol/L), there was no significant difference (P were respectively 0.427, 0.958 and 0.948, and >0.05). Results of the present experiment showed that experimental dosage of composition provided by the present disclosure did not have an obvious effect on LDL-C content in serum of SD rat.

(7) Ox-HDL contents in serum of the high, middle and low dosage groups of composition provided by the present disclosure were respectively 36.82 µg/L, 33.50 µg/L and 34.16 µg/L. Comparing with the model control group (32.90 µg/L), there was no significant difference (P were respectively 0.244, 0.864 and 0.709, and >0.05). Results of the present experiment showed that experimental dosage of composition provided by the present disclosure did not have an obvious effect on ox-HDL content in serum of SD rat.

(8) Ox-LDL-C contents in serum of the high, middle and low dosage groups of composition provided by the present disclosure were respectively 46.12 µg/L, 40.95 µg/L and 40.53 µg/L. Comparing with the model control group (44.13 µg/L), there was no significant difference (P were respectively 0.720, 0.537 and 0.472, and >0.05). Results of the present experiment showed that experimental dosage of composition provided by the present disclosure did not have an obvious effect on ox-LDL-C content in serum of SD rat.

(9) Apo-A1 contents in serum of the high, middle and low dosage groups of composition provided by the present disclosure were respectively 2800.88 µg/mL, 2621.04 µg/mL and 2434.62 µg/mL. Comparing with the model control group (2260.49 µg/mL), there was no significant difference (P were respectively 0.061, 0.251 and 0.438, and >0.05). Results of the present experiment showed that experimental dosage of composition provided by the present disclosure did not have an obvious effect on Apo-A1 content in serum of SD rat.

(10) Apo-β contents in serum of the high, middle and low dosage groups of composition provided by the present disclosure were respectively 1123.71 µg/mL, 1147.83 µg/mL and 1178.31 µg/mL. Comparing with the model control group (1023.14 µg/mL), there was no significant statistical difference (P were respectively 0.482, 0.316 and 0.188, and >0.05). Results of the present experiment showed that experimental dosage of composition provided by the present disclosure did not have an obvious effect on Apo-β content in serum of SD rat.

Combing the results above, under conditions of the present laboratory, the following conclusions were initially suggested.

Result judgment of the function of facilitating lowering blood lipid was referred to the *Technical specification for health care food inspection and evaluation* (2012 *Updated Edition*).

(1) In the present experiment, comparing the model control group with the blank control group, triglyceride content in serum increased, contents of total cholesterol and low-density lipoprotein cholesterol in serum increased, and all the differences were significant, indicating that a SD rat model of the combined hyperlipidemia was established.

(2) Comparing each dosage group of the composition provided by the present disclosure with the model control group, triglyceride in serum of the high dosage group was lowered and the difference was significant; at the same time the total cholesterol in serum and the low-density lipoprotein cholesterol of each dosage group were not significantly higher than the model control group; and the high-density lipoprotein cholesterol in serum was significantly higher than model control group. Results of the present experiments indicated that high dosage group of composition provided by the present disclosure has a function of facilitating lowering triglyceride.

Results of the present study showed that the high dosage group of the composition provided by the present disclosure can significantly increase the content of the high-density lipoprotein cholesterol content in serum of SD rat, which may inhibit the occurring of hyperlipidemia by increasing HDL-C content in serum.

In the present disclosure, all the raw materials and reagents used in the composition, method for producing the same and use thereof can be purchased on the market.

The present disclosure will be further illustrated in combination with examples.

Example 1. Preparation of Composition

| | |
|---|---|
| Inulin | 1600 g |
| Concentrated hawthorn juice (solid content 60%) | 1800 g |
| Honeysuckle extract | 110 g |
| Concentrated peach juice (solid content 60%) | 40 g |

Step 1: fresh hawthorn fruits were juiced, the filtrate was collected upon filtration and concentrated to a concentrated hawthorn juice with a solid content of 60%; the same volume of water was added to the concentrated hawthorn juice and dissolved at 85° C.; the resultant was subjected to UHT sterilization to give a first solution for use; 60% (w/w) formula amount of inulin was taken, and water 6 times (w/w) of the inulin was added, and dissolved at 85° C.; the resultant was subjected to UHT sterilization to give a second solution for use; the first solution was mixed with the second solution and subjected to freeze-drying, and the freeze-dried powders were collected and pulverized with a 40 meshes sieve to give hawthorn powders.

Step 2: fresh peach fruits were juiced, the filtrate was collected upon filtration and concentrated to obtain a concentrated peach juice with a solid content of 60%; the same volume of water was added to the concentrated peach juice and dissolved at 85° C.; the resultant was subjected to UHT sterilization to give a third solution for use; the rest amount of inulin was taken, water 6 times (w/w) of the inulin was added and dissolved at 85° C.; the resultant was subjected to UHT sterilization to give a fourth solution for use; the third solution was mixed with the fourth solution and subjected to freeze-drying, and the freeze-dried powders were collected and pulverized with a 40 meshes sieve to give peach powders.

Step 3: honeysuckle was mixed with water and subjected to extraction; the filtrate was collected upon filtration, concentrated, dried and pulverized with 80 meshes sieve to give a honeysuckle extract.

The extraction was decoction extraction; and the decoction extraction comprised two extractions, the first extraction was performed by adding water 12 times (w/w) of the starting material and extracting for 120 min, and the second extraction was performed by adding water 10 times (w/w) of the starting material and extracting for 60 min.

Step 4: the hawthorn powders obtained in Step 1, the peach powders obtained in Step 2 and the honeysuckle extract obtained in Step 3 were mixed to give the composition.

Therein, there was no restriction on the order of Step 1, Step 2 and Step 3.

Example 2. Preparation of Composition

| | |
|---|---|
| Inulin | 1200 g |
| Concentrated hawthorn juice (solid content 40%) | 2400 g |
| Honeysuckle extract | 50 g |
| Concentrated peach juice (solid content 40%) | 100 g |

Step 1: fresh hawthorn fruits were juiced, the filtrate was collected upon filtration and concentrated to a concentrated hawthorn juice with a solid content of 40%; water 3 times (w/w) of the concentrated hawthorn juice was added, and dissolved at 90° C.; the resultant was subjected to UHT sterilization to give a first solution for use; 90% (w/w) formula amount of inulin was taken, and water 5 times (w/w) of the inulin was added, and dissolved at 90° C.; the resultant was subjected to UHT sterilization to give a second solution for use; the first solution was mixed with the second solution and subjected to freeze-drying, and the freeze-dried powders were collected and pulverized with a 200 meshes sieve to give hawthorn powders.

Step 2: fresh peach fruits were juiced, the filtrate was collected upon filtration and concentrated to obtain a concentrated peach juice with a solid content of 40%; water 3 times (w/w) of the concentrated peach juice was added, and dissolved at 90° C.; the resultant was subjected to UHT sterilization to give a third solution for use; the rest amount of inulin was taken, water 5 times (w/w) of the inulin was added and dissolved at 90° C.; the resultant was subjected to UHT sterilization to give a fourth solution for use; the third solution was mixed with the fourth solution and subjected to freeze-drying, and the freeze-dried powders were collected and pulverized with a 40 meshes sieve to give peach powders.

Step 3: honeysuckle was mixed with water and subjected to extraction; the filtrate was collected upon filtration, concentrated, dried and pulverized with a 80 meshes sieve to give a honeysuckle extract.

The extraction was low-temperature high-speed countercurrent extraction, which was performed by adding water 20 times (w/w) of the starting material and extracting at 60° C. for 120 min.

Step 4: the hawthorn powders obtained in Step 1, the peach powders obtained in Step 2 and the honeysuckle extract obtained in Step 3 were mixed to give the composition.

Therein, there was no restriction on the order of Step 1, Step 2 and Step 3.

Example 3. Preparation of Composition

| | |
|---|---|
| Inulin | 2400 g |
| Concentrated hawthorn juice (solid content 70%) | 1200 g |
| Honeysuckle extract | 200 g |
| Concentrated peach juice (solid content 70%) | 20 g |

Step 1: fresh hawthorn fruits were juiced, the filtrate was collected upon filtration and concentrated to a concentrated hawthorn juice with a solid content of 70%; water 2 times (w/w) of the concentrated hawthorn juice was added, and dissolved at 80° C.; the resultant was subjected to UHT sterilization to give a first solution for use; 75% (w/w) formula amount of inulin was taken, and water 3 times (w/w) of the inulin was added, and dissolved at 80° C.; the resultant was subjected to UHT sterilization to give a second solution for use; the first solution was mixed with the second solution and subjected to freeze-drying, and the freeze-dried powders were collected and pulverized with a 120 meshes sieve to give hawthorn powders.

Step 2: fresh peach fruits were juiced, the filtrate was collected upon filtration and concentrated to obtain a concentrated peach juice with a solid content of 70%; water 2 times (w/w) of the concentrated peach juice was added, and dissolved at 80° C.; the resultant was subjected to UHT sterilization to give a third solution for use; the rest amount of inulin was taken, water 3 times (w/w) of the inulin was added and dissolved at 80° C.; the resultant was subjected to UHT sterilization to give a fourth solution for use; the third solution was mixed with the fourth solution and subjected to freeze-drying, and the freeze-dried powders were collected and pulverized with a 120 meshes sieve to give peach powders.

Step 3: honeysuckle was mixed with water and subjected to extraction; the filtrate was collected upon filtration, concentrated, dried and pulverized with a 60 meshes sieve to give a honeysuckle extract.

The extraction was ultrasonic extraction, which was performed by adding water 20 times (w/w) of the starting material and extracting at 50° C. for 90 min, and the ultrasonic frequency was 50 kHZ.

Step 4: the hawthorn powders obtained in Step 1, the peach powders obtained in Step 2 and the honeysuckle extract obtained in Step 3 were mixed to give the composition.

Therein, there was no restriction on the order of Step 1, Step 2 and Step 3.

Example 4. Preparation of Power Formulation

| | |
|---|---|
| Inulin | 1600 g |
| Concentrated hawthorn juice (solid content 60%) | 1800 g |
| Honeysuckle extract | 110 g |
| Concentrated peach juice (solid content 60%) | 40 g |
| Pectin | 45 g |
| Xylitol | 35 g |
| Stevioside | 30 g |
| Citric acid | 15 g |
| Mogroside | 6 g |

Step 1: fresh hawthorn fruits were juiced, the filtrate was collected upon filtration and concentrated to a concentrated hawthorn juice with a solid content of 60%; the same volume of water was added to the concentrated hawthorn juice and dissolved at 85° C.; the resultant was subjected to UHT sterilization to give a first solution for use; 60% (w/w) formula amount of inulin was taken, and water 6 times (w/w) of the inulin was added, and dissolved at 85° C.; the resultant was subjected to UHT sterilization to give a second solution for use; the first solution was mixed with the second solution and subjected to freeze-drying, and the freeze-dried powders were collected and pulverized with a 40 meshes sieve to give hawthorn powders.

Step 2: fresh peach fruits were juiced, the filtrate was collected upon filtration and concentrated to obtain a concentrated peach juice with a solid content of 60%; the same volume of water was added to the concentrated peach juice and dissolved at 85° C.; the resultant was subjected to UHT sterilization to give a third solution for use; the rest amount of inulin was taken, water 6 times (w/w) of the inulin was added and dissolved at 85° C.; the resultant was subjected to UHT sterilization to give a fourth solution for use; the third solution was mixed with the fourth solution and subjected to freeze-drying, and the freeze-dried powders were collected and pulverized with a 40 meshes sieve to give peach powders.

Step 3: honeysuckle was mixed with water and subjected to extraction; the filtrate was collected upon filtration, concentrated, dried and pulverized with a 60 meshes sieve to give a honeysuckle extract.

The extraction was decoction extraction; and the decoction extraction comprised two extractions, the first extraction was performed by adding water 20 times (w/w) of the starting material and extracting for 90 min, and the second extraction was performed by adding water 10 times (w/w) of the starting material and extracting for 60 min.

Step 4: the hawthorn powders obtained in Step 1, the peach powders obtained in Step 2, the honeysuckle extract obtained in Step 3 and the other ingredients were mixed to give the composition.

Therein, there was no restriction on the order of Step 1, Step 2 and Step 3.

Example 5. Preparation of Power Formulation

| | |
|---|---|
| Inulin | 1200 g |
| Concentrated hawthorn juice (solid content 40%) | 2400 g |
| Honeysuckle extract | 50 g |
| Concentrated peach juice (solid content 40%) | 100 g |
| Pectin | 30 g |
| Xylitol | 50 g |
| Stevioside | 10 g |
| Citric acid | 50 g |
| Mogroside | 5 g |

Step 1: fresh hawthorn fruits were juiced, the filtrate was collected upon filtration and concentrated to a concentrated hawthorn juice with a solid content of 40%; water 3 times (w/w) of the concentrated hawthorn juice was added, and dissolved at 90° C.; the resultant was subjected to UHT sterilization to give a first solution for use; 90% (w/w) formula amount of inulin was taken, and water 5 times (w/w) of the inulin was added, and dissolved at 90° C.; the resultant was subjected to UHT sterilization to give a second solution for use; the first solution was mixed with the second solution and subjected to freeze-drying, and the freeze-dried powders were collected and pulverized with a 200 meshes sieve to give hawthorn powders.

Step 2: fresh peach fruits were juiced, the filtrate was collected upon filtration and concentrated to obtain a concentrated peach juice with a solid content of 40%; water 3 times (w/w) of the concentrated peach juice was added, and dissolved at 90° C.; the resultant was subjected to UHT sterilization to give a third solution for use; the rest amount of inulin was taken, water 5 times (w/w) of the inulin was added and dissolved at 90° C.; the resultant was subjected to UHT sterilization to give a fourth solution for use; the third solution was mixed with the fourth solution and subjected to freeze-drying, and the freeze-dried powders were collected and pulverized with a 200 meshes sieve to give peach powders.

Step 3: honeysuckle was mixed with water and subjected to extraction; the filtrate was collected upon filtration, concentrated, dried and pulverized with a 60 meshes sieve to give a honeysuckle extract.

The extraction was low-temperature high-speed countercurrent extraction, which was performed by adding water 20 times (w/w) of the starting material and extracting at 40° C. for 120 min.

Step 4: the hawthorn powders obtained in Step 1, the peach powders obtained in Step 2, the honeysuckle extract obtained in Step 3 and the other ingredients were mixed to give the composition.

Therein, there was no restriction on the order of Step 1, Step 2 and Step 3.

Example 6. Preparation of Power Formulation

| | |
|---|---|
| Inulin | 2400 g |
| Concentrated hawthorn juice (solid content 70%) | 1200 g |
| Honeysuckle extract | 200 g |
| Concentrated peach juice (solid content 70%) | 20 g |
| Pectin | 50 g |
| Xylitol | 25 g |
| Stevioside | 50 g |
| Citric acid | 10 g |
| Mogroside | 15 g |

Step 1: fresh hawthorn fruits were juiced, the filtrate was collected upon filtration and concentrated to a concentrated hawthorn juice with a solid content of 70%; water 2 times (w/w) of the concentrated hawthorn juice was added, and dissolved at 80° C.; the resultant was subjected to UHT sterilization to give a first solution for use; 75% (w/w) formula amount of inulin was taken, and water 3 times (w/w) of the inulin was added, and dissolved at 80° C.; the resultant was subjected to UHT sterilization to give a second solution for use; the first solution was mixed with the second solution and subjected to freeze-drying, and the freeze-dried powders were collected and pulverized with a 120 meshes sieve to give hawthorn powders.

Step 2: fresh peach fruits were juiced, the filtrate was collected upon filtration and concentrated to obtain a concentrated peach juice with a solid content of 70%; water 2 times (w/w) of the concentrated peach juice was added, and dissolved at 80° C.; the resultant was subjected to UHT sterilization to give a third solution for use; the rest amount of inulin was taken, water 3 times (w/w) of the inulin was added and dissolved at 80° C.; the resultant was subjected to UHT sterilization to give a fourth solution for use; the third solution was mixed with the fourth solution and subjected to freeze-drying, and the freeze-dried powders were collected and pulverized with a 120 meshes sieve to give peach powders.

Step 3: honeysuckle was mixed with water and subjected to extraction; the filtrate was collected upon filtration, concentrated, dried and pulverized with a 60 meshes sieve to give a honeysuckle extract.

The extraction was ultrasonic extraction, which was performed by adding water 12 times (w/w) of the starting material and extracting at 60° C. for 120 min, and the ultrasonic frequency was 50 kHZ.

Step 4: the hawthorn powders obtained in Step 1, the peach powders obtained in Step 2, the honeysuckle extract obtained in Step 3 and the other ingredients were mixed to give the composition.

Therein, there was no restriction on the order of Step 1, Step 2 and Step 3.

Comparative Example

| | |
|---|---|
| Maltodextrin | 1600 g |
| Concentrated hawthorn juice (solid content 70%) | 1800 g |
| Honeysuckle extract | 110 g |
| Concentrated peach juice (solid content 70%) | 40 g |
| Pectin | 45 g |
| Xylitol | 35 g |
| Stevioside | 30 g |
| Citric acid | 15 g |
| Mogroside | 6 g |

Step 1: fresh hawthorn fruits were juiced, the filtrate was collected upon filtration and concentrated to a concentrated hawthorn juice with a solid content of 70%; water 2 times (w/w) of the concentrated hawthorn juice was added, and dissolved at 80° C.; the resultant was subjected to UHT sterilization to give a first solution for use; 60% (w/w) formula amount of maltodextrin was taken, and water 3 times (w/w) of the inulin was added, and dissolved at 80° C.; the resultant was subjected to UHT sterilization to give a second solution for use; the first solution was mixed with the second solution and subjected to freeze-drying, and the freeze-dried powders were collected and pulverized with a 40 meshes sieve to give hawthorn powders.

Step 2: fresh peach fruits were juiced, the filtrate was collected upon filtration and concentrated to obtain a concentrated peach juice with a solid content of 70%; water 2 times (w/w) of the concentrated peach juice was added, and dissolved at 80° C.; the resultant was subjected to UHT sterilization to give a third solution for use; the rest amount of inulin was taken, water 3 times (w/w) of the inulin was added and dissolved at 80° C.; the resultant was subjected to UHT sterilization to give a fourth solution for use; the third solution was mixed with the fourth solution and subjected to freeze-drying, and the freeze-dried powders were collected and pulverized with a 40 meshes sieve to give peach powders.

Step 3: honeysuckle was mixed with water and subjected to extraction; the filtrate was collected upon filtration, concentrated, dried and pulverized with a 60 meshes sieve to give a honeysuckle extract.

The extraction was ultrasonic extraction, which was performed by adding water 12 times (w/w) of the starting material and extracting at 40° C. for 120 min, and the ultrasonic frequency was 20 kHZ.

Step 4: the hawthorn powders obtained in Step 1, the peach powders obtained in Step 2, the honeysuckle extract obtained in Step 3 and the other ingredients were mixed to give the composition.

Therein, there was no restriction on the order of Step 1, Step 2 and Step 3.

Example 7. Experiments

Materials and Method
1. Experiment Materials
1.1 Experimental Animal
  Name: SPF grade male SD rats, body weight 170~220 g
  Source: Supplied by Animal Center of Southern Medical University, License No. SCXK (Yue) 2016-0041
  High-fat diet: maintenance diet with 20.0% sucrose, 15% lard, 1.2% cholesterol, 0.2% sodium cholate, appropriate amounts of casein, calcium hydrogen phosphate, rock powders and so on. Except for crude fat, water content, crude protein, crude fat, crude fiber, ash, calcium, phosphate and calcium:phosphate ratio reached the national standard for maintenance diet.
  Housing model: housing in a barrier environment.
1.2 Equipment and Reagents
  Surgical instruments, centrifuges, centrifuge tubes, electronic balances, punchers, gavage needles, enzyme-labeled instruments, heparin sodium, anesthetic, formalin, refrigerators, vortex mixer, weighing scale, serum total cholesterol (TC) ELISA kit, serum triglyceride (TG) ELISA kit, serum high-density lipoprotein cholesterol (HDL-C) ELISA kit, serum low-density lipoprotein cholesterol (LDL-C) ELISA kit, serum oxidized high-density lipoprotein cholesterol (ox-HDL-C) ELISA kit, serum oxidized low-density lipoprotein cholesterol (ox-LDL-C) ELISA kit, serum apolipoprotein A1 (apo-A1) ELISA kit, and serum apolipoprotein (apo-$\beta$) ELISA kit.
1.3 Other Materials
  Gloves, disposable masks, alcohol, ear tags, tag papers, syringes and so on.
2. Design of Experiment
2.1 Grouping of the Animals
  There were three dosage groups, two positive control groups, one blank control group and one model control group. In low-dosage group, the test sample was administered at a dosage of 5 times of the recommendation amount for human (500 mg/kg), and in middle-dosage and high-dosage groups, the dosages equaled to 10 times (1000 mg/kg) and 25 times (2500 mg/kg) of the recommendation amount for human. The dosage of the positive control group equaled to 5 times (omega: 150 mg/kg; and atorvastatin calcium: 0.83 mg/kg) of the recommendation amount for human. The blank control group and the model control group were administered with equal amount of distilled water at the same volume by gavage. The duration of the administration of the test sample was generally 30 days.
2.2 Preparation of the Test Sample
  The compositions provided by the examples 1~3, the powder formulations provided by the examples 4~6 were accurately weighed, and an appropriate amount of distilled water was added to prepare the low-, middle- and high-dosages samples. The samples were prepared right before use.
2.3 Test Indexes
  (1) Body weight;
  (2) Total cholesterol (TC) in serum;
  (3) Triglyceride (TG) in serum;
  (4) High-density lipoprotein cholesterol (HDL-C) in serum;
  (5) Low-density lipoprotein cholesterol (LDL-C) in serum;
  (6) Oxidized high-density lipoprotein cholesterol (ox-HDL-C) in serum;
  (7) Oxidized low-density lipoprotein cholesterol (ox-LDL-C) in serum;
  (8) Apolipoprotein A1 (apo-A1) in serum;
  (9) Apolipoprotein beta (apo-beta) in serum.
3. Experiment Method
  (1) Adaptive period: In a barrier system, the rats were fed on maintenance diet and observed for 5~7 days.
  (2) Model-establishing period:
  The rats were randomly divided into 22 groups, 6 per group. One group was fed on the maintenance diet as the blank control group. The other 21 groups were fed on high-fat diet as the model control group. The rats were weighed once a week.

20 days after the model control group was fed on high-fat diet, rats in the blank control group and the model control groups were subjected to blood collection (1~1.5 mL of blood was collected from the tail vein) without fasting. After blood collection, the serum was quickly separated to a new centrifugal tube, stored at −20° C. before test. Levels of TC, TG, LDL-C, HDL-C in serum were tested with cholesterol, triglycerides, high-density lipoprotein cholesterol and low-density lipoprotein cholesterol ELISA kits. According to the TC level and the number of the test samples, the model control groups were randomly divided into one model group, one Omega group, one atorvastatin group and 6 large test sample groups, and each large test sample group has 3 dosage groups.

(3) Administration of Test Sample

After grouping, each dosage group was orally administered with the test sample every day, the two positive groups were respectively orally administered with positive control samples (diluted Omega solution and diluted atorvastatin calcium solution), and the blank control group and the model control group were administered with the same volume of distilled water. The blank control group was continuously fed with maintenance diet. The positive control group, model control group and the dosage groups of the test samples were continuously fed with high-fat diet. All rats were weighed regularly. At the end of the experiment, without fasting, blood samples were collected from eyeballs of the rats. After blood collection, the serum was quickly separated, and levels of TC, TG, HDL-C, LDL-C, ox-HDL-C, ox-LDL-C, apo-A1 and apo-β in serum were measured.

4. Data Analysis and Results Evaluation

The data was processed by analysis of variance. However, according to the process of analysis of variance, a homogeneity test of variance was carried out firstly. If the variance was homogenous, the F value was calculated. When the F value is F<0.05, the differences of the means of each group were not significant. When the F value is F≥0.05, and P≤0.05, statistics were performed by a pairwise comparison between means of multiple experimental groups and one control group; appropriate variable conversion was performed on non-homogenous data. After the data meet the requirement of normality or homogeneity of variance, statistic was performed on the converted data. If the converted data still could not achieve normality or homogeneity, the statistic was carried out by method of rank sum test.

Reference was made to the *Technical specification for health care food inspection and evaluation* (2012 *Updated Edition*), and judgment was made according to the following standards.

Evaluation of function of facilitating lowering blood lipid: comparing the model control group with the blank control group, triglyceride in serum increased, total cholesterol and low-density lipoprotein cholesterol in serum increased and all the differences were significant, indicating that the model was established.

(1) Comparing each dosage group with the model control group, if total cholesterol or low-density lipoprotein cholesterol in serum of any dosage group decreased, triglyceride in serum of any dosage group decreased, and the differences were significant, meanwhile high-density lipoprotein cholesterol in serum of each dosage group was not significantly lower than that of the model control group, it can be considered that the result of facilitating lowering blood lipid in animal experiment was positive.

(2) Comparing each dosage group with the model control group, if total cholesterol or low-density lipoprotein cholesterol in serum of any dosage group decreased, and the differences were significant, meanwhile, triglyceride in serum of each dosage group was not significantly higher than that of the model control group, and high-density lipoprotein cholesterol in serum of each dosage group was not significantly lower than that of the model control group, it can be considered that the result of facilitating lowering cholesterol in animal experiment was positive.

(3) Comparing each dosage group with the model control group, if triglyceride in serum of any dosage group decreased, and the differences were significant, meanwhile, total cholesterol and low-density lipoprotein cholesterol in serum of each dosage group was not significantly higher than that of the model control group, and high-density lipoprotein cholesterol in serum was not significantly lower than that of the model control group, it can be considered that the result of facilitating lowering triglyceride in animal experiment was positive.

5. Results of Experiments on Functions of Facilitating Lowering Blood Lipid by the Composition and Powder Formulations Provided by the Present Disclosure (1) Establishment of Combined Hyperlipidemia Rat Model

TABLE 1

Levels of TG, TC, HDL-C and LDL-C in serum of the SD rats of combined hyperlipidemia model

| Group | Mean Value ± Standard Deviation (μmol/L) | | | |
|---|---|---|---|---|
| | TG | TC | HDL-C | LDL-C |
| Blank Group | 146.20 ± 14.73 | 936.47 ± 30.67 | 727.84 ± 123.11 | 810.07 ± 60.36 |
| Model Group | 190.62 ± 24.59** | 1148.96 ± 107.94** | 734.66 ± 40.59 | 947.36 ± 89.29* |

Comment: comparing the model group with the blank group, * indicates P < 0.05, and ** indicates P < 0.01.

Results in Table 1 and FIG. 1 showed that TC content was 936.47 μmol/L in serum of the blank control group and 1148.96 μmol/L in the model control group; comparing with the blank control group (P=0.004, <0.01), the difference was significant. TG content was 146.20 μmol/L in the blank control group and 190.62 μmol/L in the model control group; comparing with the blank control group (P=0.005, <0.01), the difference was significant. HDL-C content in the serum was 727.84 μmol/L in the blank control group and 734.66 μmol/L in the model control group; comparing with the blank control group (P=0.902, >0.05), the difference was not significant. LDL-C content in the serum was 810.07 μmol/L in the blank control group and 947.36 μmol/L in the model control group; comparing with the blank control group (P=0.013, <0.05), the difference was significant. Comparing the model control group with the blank control group, the TG content in serum increased, the contents of TC and LDL-C in serum also increased, and all the differences were significant, demonstrating that combined hyperlipidemia rat model was established successfully.

TABLE 2

Levels of Ox-HDL-C, Ox-LDL-C, Apo-A1 and Apo-β in serum of SD rats of combined hyperlipidemia model

| Group | Mean Value ± Standard Deviation (μg/L) | | Mean Value ± Standard Deviation (μg/mL) | |
|---|---|---|---|---|
| | Ox-HDL-C | Ox-LDL-C | Apo-A1 | Apo-β |
| Blank Group | 32.41 ± 4.29 | 36.51 ± 3.04 | 2271.27 ± 237.59 | 882.53 ± 64.32 |
| Model Group | 32.90 ± 4.65 | 44.12 ± 6.25* | 2260.49 ± 201.25 | 1023.14 ± 101.20* |

Comment: comparing the model group with the blank group, * indicates P < 0.05, and ** indicates P < 0.01.

Figure 2:
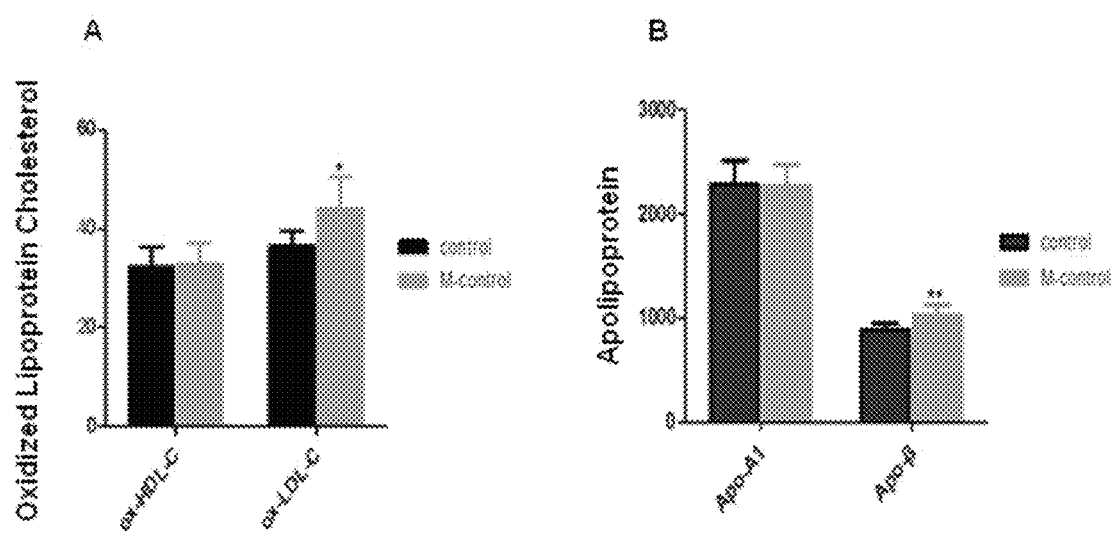
FIG. 2 shows levels of oxidized lipoprotein cholesterol and two apolipoproteins in the serum of the blank group and model group of SD rats; and * indicates comparing the model group with the blank group, * indicates P<0.05, and ** indicates P<0.01.

Results of Table 2 and FIG. 2 showed that ox-HDL-C content in serum of the high-fat model group and the blank control group were not significantly different (P=0.853, >0.05). However, ox-LDL-C content of the blank group was 36.51 μg/L, and the high-fat model group was 44.12 μg/L. Ox-LDL-C content in serum of the high-fat model group significantly increased (P=0.030, <0.05). Apo-A1 content of the blank group was 2271.27 μg/L, and the high-fat model group was 2260.49 μg/L. Apo-A1 content in serum was not significantly changed (P=0.934, >0.05). Comparing the high-fat model group with the blank group, Apo-β content in serum was significantly different (P=0.020, <0.05).

(2) Effects of the Composition and Powder Formulation Provided by the Present Disclosure on Weights of SD Rats

TABLE 3

Weights of SD rats in each group before administration of test sample

| Group | | Initial Weight (Mean Value ± Standard Deviation) | Final Weight (Mean Value ± Standard Deviation) |
|---|---|---|---|
| Control | | 321.50 ± 22.74 | 385.00 ± 26.93* |
| M-Control | | 334.50 ± 22.87 | 410.67 ± 30.71 |
| Example 1 | H | 348.67 ± 30.02 | 415.00 ± 36.07 |
| | M | 333.33 ± 35.90 | 402.33 ± 35.07 |
| | L | 353.17 ± 41.48 | 408.50 ± 33.87 |
| Example 2 | H | 343.15 ± 31.27 | 401.53 ± 40.37 |
| | M | 341.84 ± 37.69 | 413.74 ± 32.27 |
| | L | 340.53 ± 30.71 | 416.27 ± 34.17 |
| Example 3 | H | 339.45 ± 35.48 | 406.57 ± 38.42 |
| | M | 338.29 ± 409 | 411.51 ± 39.88 |
| | L | 335.33 ± 32.08 | 414.48 ± 33.07 |
| Example 4 | H | 347.57 ± 38.49 | 411.35 ± 37.28 |
| | M | 345.23 ± 35.61 | 405.74 ± 33.64 |
| | L | 349.13 ± 37.58 | 418.37 ± 33.24 |
| Example 5 | H | 338.56 ± 30.17 | 410.97 ± 30.24 |
| | M | 335.68 ± 32.41 | 410.57 ± 35.12 |
| | L | 335.17 ± 35.45 | 404.28 ± 34.15 |
| Example 6 | H | 345.62 ± 35.45 | 398.35 ± 34.66 |
| | M | 347.26 ± 33.52 | 405.17 ± 35.42 |
| | L | 342.18 ± 37.89 | 411.48 ± 34.57 |
| Comparative Example | H | 341.75 ± 41.22 | 408.34 ± 38.59 |
| | M | 347.05 ± 38.04 | 415.67 ± 35.28 |
| | L | 345.48 ± 35.33 | 407.39 ± 37.41 |
| Omega | | 332.17 ± 35.53 | 392.67 ± 39.66 |
| Atorvastatin Calcium | | 339.17 ± 23.07 | 442.00 ± 40.77 |

Figure 3:
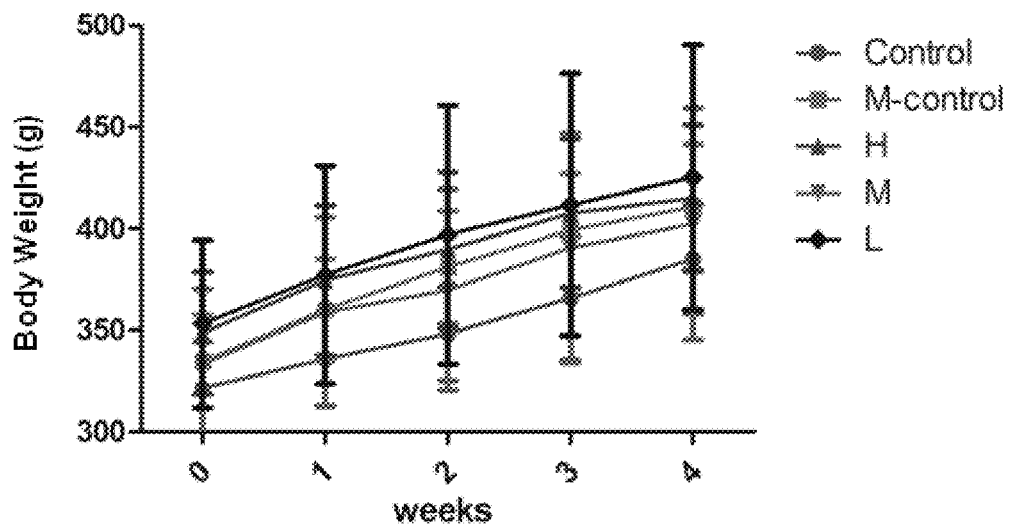
FIG. 3 shows influences of the composition provided by the present disclosure on the body weights of SD rats.

Results of Table 3 and FIG. 3 showed that weight growth of dosage groups and model control group, which were fed with high-fat diet, was significantly faster than that of the blank control group fed with maintenance diet. However, there was no significant difference between weight of each dosage group and the model control group. Results of the experiment showed that the composition and the powder formulations provided by the present disclosure did not have an obvious effect on weight of SD rats.

(3) Effects of the Composition and Powder Formulation Provided by the Present Disclosure on Level of Total Cholesterol (TC) in Serum of SD Rats

TABLE 4

TC levels in serum of animals in each group

| Group | | Mean Value ± Standard Deviation |
|---|---|---|
| M-Control | | 1148.96 ± 107.94 |
| Control | | 936.47 ± 30.67** |
| Example 1 | H | 1168.54 ± 111.29 |
| | M | 1159.86 ± 149.98 |
| | L | 1184.54 ± 121.77 |
| Example 2 | H | 1136.25 ± 127.34 |
| | M | 1152.35 ± 135.89 |
| | L | 1158.28 ± 111.96 |
| Example 3 | H | 1142.59 ± 124.59 |
| | M | 1163.27 ± 132.57 |
| | L | 1153.85 ± 111.27 |
| Example 4 | H | 1161.49 ± 125.86 |
| | M | 1174.59 ± 134.28 |
| | L | 1152.37 ± 114.95 |
| Example 5 | H | 1156.78 ± 111.74 |
| | M | 1153.29 ± 117.27 |
| | L | 1177.59 ± 128.47 |
| Example 6 | H | 1184.59 ± 127.58 |
| | M | 1143.48 ± 147.25 |
| | L | 1169.53 ± 117.67 |
| Comparative Example | H | 1152.67 ± 105.49 |
| | M | 1143.54 ± 127.94 |
| | L | 1178.84 ± 137.12 |
| Omega | | 1209.43 ± 105.23 |
| Atorvastatin Calcium | | 1117.14 ± 171.07 |

Comment: comparing the high-fat model group with the blank group, ** indicates P < 0.01, and * indicates P < 0.05.

Figure 4:
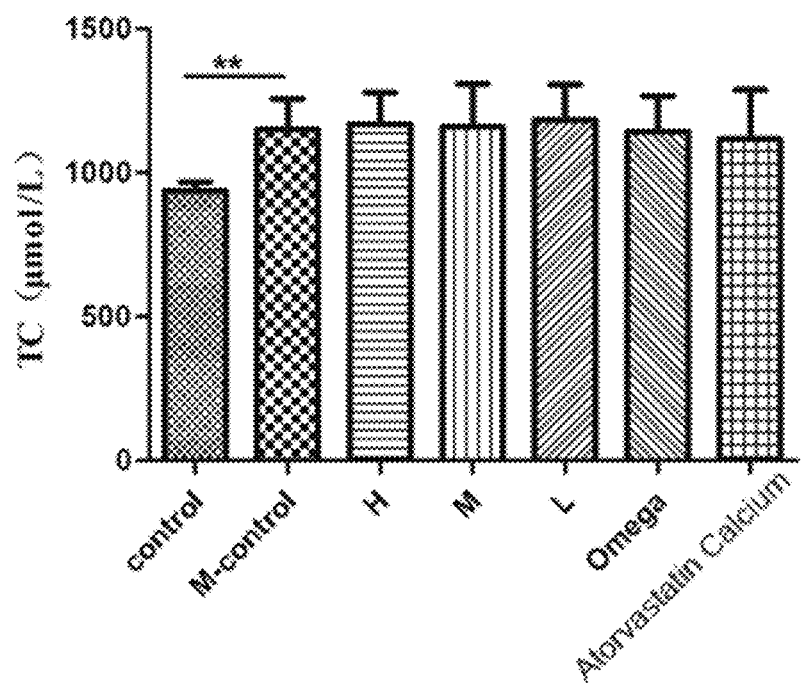
FIG. 4 shows influences of the composition provided by the present disclosure on TC content in the serum of SD rats; and * indicates comparing the high-fat model group with the blank group, wherein ** indicates P<0.01; and * indicates P<0.05.

Results of Table 4 and FIG. 4 showed that total cholesterol (TC) contents in the high, middle and low dosage groups of the composition and powder formulation provided by the present disclosure were respectively 1168.54 μmol/L, 1159.86 μmol/L and 1184.54 μmol/L. Comparing with the model control group (1148.96 μmol/L), there was no significantly difference after a statistical analysis (P>0.05). Comparing each dosage group with the Omega group and the atorvastatin calcium control group, there was no significant difference (P were respectively 0.528, 0.524, 0.713, 0.553, 0.656 and 0.452, >0.05). Results of the present experiment showed that the composition and powder formulation provided by the present disclosure did not have an obvious effect on TC content in serum of SD rats.

Comparing the results of the example 1~6 with that of the same dosage group of the comparative example, the results of the example 1~6 were lower, but there was no significant difference (P<0.05).

(4) Effects of the Composition and Powder Formulation Provided by the Present Disclosure on Level of Triglyceride (TG) in Serum of SD Rats

TABLE 5

TG levels in serum of animals in each group

| Group | | Mean Value ± Standard Deviation |
|---|---|---|
| M-control | | 190.62 ± 24.58 |
| Control | | 146.20 ± 14.73** |
| Example 1 | H | 154.96 ± 27.65# |
| | M | 195.92 ± 31.33 |
| | L | 208.59 ± 38.46 |
| Example 2 | H | 157.34 ± 24.65# |
| | M | 188.3 ± 33.94 |
| | L | 197.54 ± 33.55 |
| Example 3 | H | 161.25 ± 20.21# |
| | M | 188.42 ± 34.58 |
| | L | 192.63 ± 30.11 |
| Example 4 | H | 154.84 ± 29.39# |
| | M | 185.59 ± 30.26 |
| | L | 198.91 ± 37.85 |
| Example 5 | H | 160.33 ± 21.29# |
| | M | 192.24 ± 29.05 |
| | L | 203.31 ± 38.79 |
| Example 6 | H | 158.37 ± 30.39# |
| | M | 191.71 ± 33.52 |
| | L | 206.39 ± 32.26 |
| Comparative Example | H | 165.39 ± 25.63# |
| | M | 205.48 ± 33.92 |
| | L | 195.35 ± 34.97 |
| Omega | | 198.77 ± 31.65 |
| Atorvastatin Calcium | | 189.71 ± 45.83 |

Comment: when comparing the high-fat model group with the blank group, wherein ** indicates P < 0.01, and * indicates P < 0.05; when comparing each experiment group with the high-fat model group, ## indicates P < 0.01, and # indicates P < 0.05.

Figure 5:
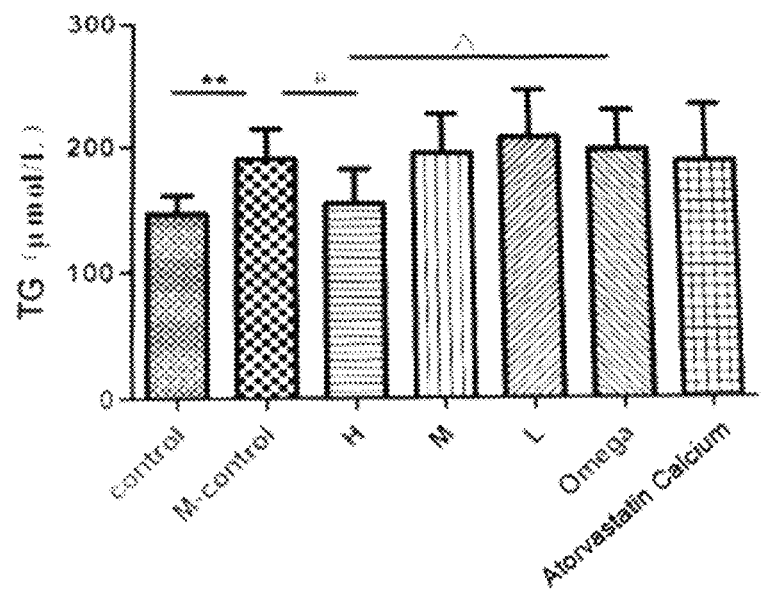
FIG. 5 shows influences of the composition provided by the present disclosure on TG content in the serum of SD rats; * indicates comparing the high-fat model group with the blank group, wherein ** indicates P<0.01; * indicates P<0.05; # indicates comparing each dosage group with the high-fat model group, and ## indicates P<0.01; # indicates P<0.05; Δ indicates comparing each dosage group with the Omega phase, and ΔΔ indicates P<0.01; and A indicates P<0.05.

Results of Table 5 and FIG. 5 showed that triglyceride (TG) content in serum of the high dosage group of composition and powder formulation provided by the present disclosure was 154.96 µmol/L, and there was a significant difference (P=0.040, <0.05) comparing with the model control group (190.62 µmol/L). TG contents in serums of the middle and low dosage groups were respectively 195.92 µmol/and 208.59 µmol/L, and there was no significant difference (P were respectively 0.751 and 0.352, >0.05) comparing with the model control group. Results of the experiment showed that the composition and powder formulation provided by the present disclosure significantly decreased TG content in serum of SD rats. Comparing each dosage group with the Omega control group, TG level of the high dosage group of the test sample was significantly lower than that of the Omega control group (P=0.029, <0.05), but there was no significant difference in the middle and low dosage groups (P were respectively 0.878 and 0.640, >0.05). Comparing each dosage groups of the test sample with the atorvastatin calcium control group, TG levels of each dosage group of the test sample was not significantly different (P were respectively 0.149, 0.790 and 0.458, >0.05).

Comparing the example 1~6 with the same dosage group of the comparative example, each dosage group did not have significant difference, but TG levels in the high dosage groups of the examples were lower. Effect of the examples on lowering triglyceride in serum was equal or better than that of the comparative example.

(5) Effects of the Composition and Powder Formulation Provided by the Present Disclosure on Level of High-Density Lipoprotein Cholesterol (HDL-C) in Serum of SD Rats

TABLE 6

HDL-C levels in serum of animals in each group

| Group | | Mean Value ± Standard Deviation |
|---|---|---|
| M-control | | 734.66 ± 40.59 |
| Control | | 727.84 ± 123.11 |
| Example 1 | H | 849.23 ± 101.24# |
| | M | 853.90 ± 236.52 |
| | L | 861.74 ± 239.69 |
| Example 2 | H | 851.26 ± 157.29# |
| | M | 855.93 ± 240.08 |
| | L | 865.39 ± 231.17 |
| Example 3 | H | 847.92 ± 112.33# |
| | M | 850.91 ± 243.77 |
| | L | 862.94 ± 245.58 |
| Example 4 | H | 851.35 ± 133.76# |
| | M | 854.79 ± 221.74 |
| | L | 865.46 ± 233.65 |
| Example 5 | H | 852.27 ± 129.83# |
| | M | 856.74 ± 219.03 |
| | L | 864.33 ± 248.74 |
| Example 6 | H | 847.91 ± 135.74# |
| | M | 856.73 ± 224.73 |
| | L | 867.74 ± 235.64 |
| Comparative Example | H | 857.49 ± 125.46# |
| | M | 871.24 ± 253.29 |
| | L | 883.46 ± 241.19 |
| Omega | | 815.14 ± 230.24 |
| Atorvastatin Calcium | | 919.74 ± 150.63# |

Comment: when comparing the high-fat model group with the blank group, wherein ** indicates P < 0.01, and * indicates P < 0.05; when comparing each experiment group with the high-fat model group, ## indicates P < 0.01, and # indicates P < 0.05.

Figure 6:
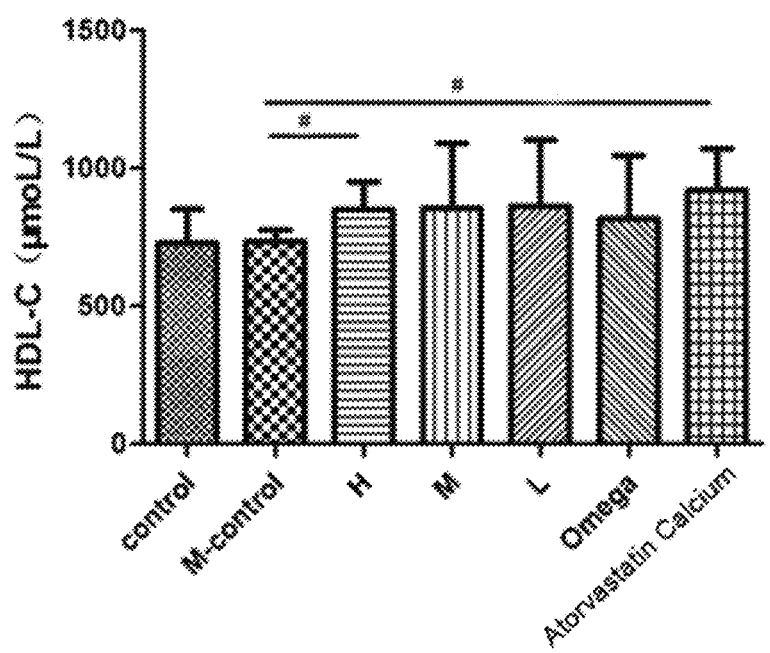
FIG. 6 shows influences of the composition provide by the present disclosure on HDL-C content in the serum of SD rats; * indicates comparing the high-fat model group with the blank group, wherein ** indicates P<0.01; * indicates P<0.05; # indicates comparing each experiment group with the high-fat model group, and ## indicates P<0.01; and # indicates P<0.05.

Results of Table 6 and FIG. 6 showed that HDL-C content of high dosage group of the composition and powder formulation provided by the present disclosure was 849.23 µmol/L, and there was a significant difference (P=0.039, <0.05) comparing with the model control group (734.66 µmol/L). HDL-C content of middle dosage group was 853.90 µmol/L, and there was no significant difference (P=0.275, >0.05) comparing with the model control group. HDL-C content of low dosage group was 861.74 µmol/L, and there was no significant difference (P=0.254, >0.05) comparing with the model control group. Comparing each dosage group of the test sample with the Omega group and the atorvastatin calcium group, there was no significant difference. Results of the present disclosure showed that the composition and the powder formulation provided by the present disclosure significantly increased HDL-C content in serum of SD rat. It was reported in the literature that HDL (high-density lipoprotein) can enter and exit the arterial wall freely, and maliciously ingest harmful substances such as low-density lipoprotein and triglyceride deposited at the bottom of the vascular wall, which resisted the oxidized of low-density lipoprotein by reverse cholesterol transportation.

Comparing the results of the example 1~6 with that of the same dosage group of the comparative example, there was no significant difference (P>0.05).

(6) Effects of the Composition and Powder Formulation Provided by the Present Disclosure on Level of Low-Density Lipoprotein Cholesterol (LDL-C) in Serum of SD Rats

TABLE 7

LDL-C levels in serum of animals in each group

| Group | | Mean Value ± Standard Deviation |
|---|---|---|
| M-control | | 947.35 ± 89.29 |
| Control | | 810.07 ± 60.35* |
| Example 1 | H | 870.88 ± 203.10 |
| | M | 943.29 ± 161.18 |
| | L | 941.32 ± 199.24 |
| Example 2 | H | 868.39 ± 198.07 |
| | M | 941.02 ± 159.83 |
| | L | 945.37 ± 194.83 |
| Example 3 | H | 872.93 ± 168.49 |
| | M | 940.35 ± 178.53 |
| | L | 947.29 ± 210.23 |
| Example 4 | H | 873.25 ± 197.39 |
| | M | 941.04 ± 156.39 |
| | L | 950.17 ± 189.58 |
| Example 5 | H | 872.35 ± 201.45 |
| | M | 944.93 ± 150.34 |
| | L | 950.26 ± 210.39 |
| Example 6 | H | 865.43 ± 210.33 |
| | M | 948.37 ± 174.18 |
| | L | 951.23 ± 201.22 |
| Comparative Example | H | 882.29 ± 193.46 |
| | M | 961.03 ± 154.33 |
| | L | 970.26 ± 201.93 |
| Omega | | 945.27 ± 139.88 |
| Atorvastatin Calcium | | 853.24 ± 235.19 |

Comment: comparing the high-fat model group with the blank group, wherein ** indicates $P < 0.01$, and * indicates $P < 0.05$.

Figure 7:
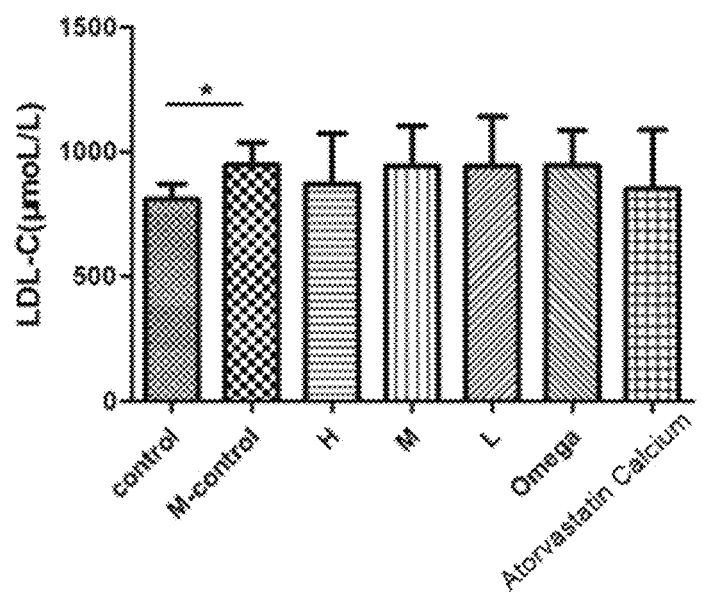
FIG. 7 shows influences of the composition provided by the present disclosure on LDL-C in the serum of SD rats; * indicates comparing the high-fat model group with the blank group, wherein ** indicates P<0.01; and * indicates P<0.05.

Results of Table 7 and FIG. 7 showed that LDL-C contents in serum of the high, middle and low dosage groups of composition and powder formulation provided by the present disclosure were respectively 870.88 µmol/L, 943.29 µmol/L and 941.32 µmol/L. Comparing with the model control group (947.36 µmol/L), there was no significant difference (P were respectively 0.427, 0.958 and 0.948, >0.05). Comparing each dosage group with the Omega group and the atorvastatin calcium group, there was also no significant difference (P were respectively 0.479, 0.982, 0.969 and 0.892, d>0.05). Results of the experiment showed that the composition and powder formulation provided by the present disclosure did not have an obvious effect on LDL-C content in serum of SD rats.

Comparing results of the example 1~6 with that of the same dosage group of the comparative example, there was no significant difference (P>0.05).

(7) Effects of the Composition and Powder Formulation Provided by the Present Disclosure on Level of Oxidized High-Density Lipoprotein Cholesterol (Ox-HDL-C) in Serum of SD Rats

TABLE 8

Ox-HDL-C levels in serum of animals in each group

| Group | | Mean Value ± Standard Deviation |
|---|---|---|
| M-control | | 32.90 ± 4.65 |
| Control | | 32.41 ± 4.29 |
| Example 1 | H | 36.82 ± 6.18 |
| | M | 33.50 ± 6.81 |
| | L | 34.16 ± 6.47 |
| Example 2 | H | 35.15 ± 6.04 |
| | M | 33.71 ± 5.97 |
| | L | 35.69 ± 5.94 |
| Example 3 | H | 35.35 ± 6.03 |
| | M | 34.75 ± 5.99 |
| | L | 34.57 ± 6.12 |

TABLE 8-continued

Ox-HDL-C levels in serum of animals in each group

| Group | | Mean Value ± Standard Deviation |
|---|---|---|
| Example 4 | H | 35.73 ± 5.94 |
| | M | 34.54 ± 6.29 |
| | L | 33.94 ± 5.34 |
| Example 5 | H | 37.20 ± 6.32 |
| | M | 34.57 ± 6.23 |
| | L | 34.27 ± 5.94 |
| Example 6 | H | 35.25 ± 7.21 |
| | M | 34.85 ± 6.13 |
| | L | 35.14 ± 6.57 |
| Comparative Example | H | 34.28 ± 7.35 |
| | M | 32.48 ± 6.33 |
| | L | 34.37 ± 6.84 |
| Omega | | 39.08 ± 2.97 |
| Atorvastatin Calcium | | 35.88 ± 7.30 |

Comment: comparing each experiment group with the high-fat model group, ## indicates $P < 0.01$, and # indicates $P < 0.05$.

Figure 8:
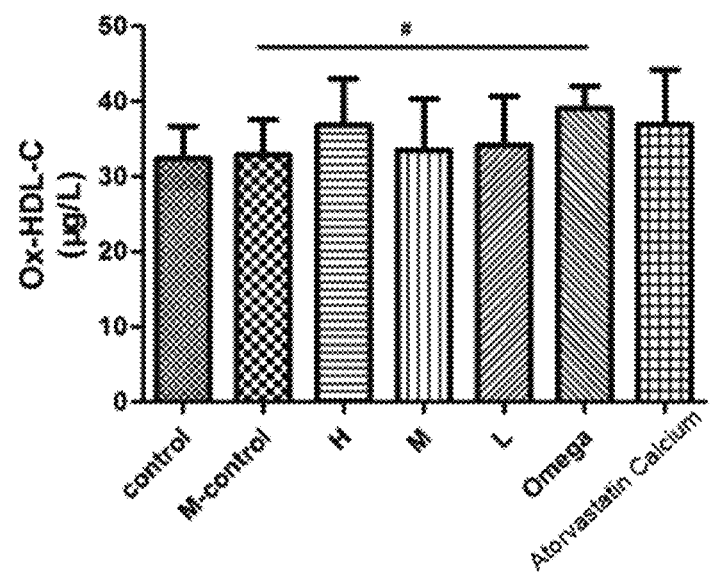
FIG. 8 shows influences of the composition provided by the present disclosure on ox-HDL content in the serum of SD rats; # indicates comparing each experiment group with the high-fat model group, and ## indicates P<0.01; and # indicates P<0.05.

Results of Table 8 and FIG. 8 showed that ox-HDL-C contents in serum of the high, middle and low dosage groups of the composition and powder formulation provided by the present disclosure were respectively 36.82 µg/L, 33.50 µg/L and 34.16 µg/L. Comparing with the model control group (32.90 µg/L), there was no significant difference (P were respectively 0.244, 0.864 and 0.709, >0.05). Comparing each dosage group with the Omega group and the atorvastatin group, there was no significant difference (P were respectively 0.448, 0.110, 0.134 and 0.989, 0.426 and 0.510, >0.05). Results of the present experiment showed that the composition and powder formulation provided by the present disclosure did not have an obvious effect of ox-HDL content in serum of SD rat.

Comparing the results of example 1~6 with that of the same dosage group of the comparative example, there was no significant difference (P>0.05).

(8) Effects of the Composition and Powder Formulation Provided by the Present Disclosure on Level of Oxidized Low-Density Lipoprotein Cholesterol (Ox-LDL-C) in Serum of SD Rats

TABLE 9

Ox-LDL-C levels in serum of animals in each group

| Group | | Mean Value ± Standard Deviation |
|---|---|---|
| M-control | | 44.13 ± 6.25 |
| Control | | 36.51 ± 3.04* |
| Example 1 | H | 46.12 ± 11.50 |
| | M | 40.95 ± 10.30 |
| | L | 40.53 ± 9.90 |
| Example 2 | H | 45.75 ± 10.94 |
| | M | 40.25 ± 9.35 |
| | L | 40.2 ± 10.38 |
| Example 3 | H | 44.74 ± 10.84 |
| | M | 40.78 ± 10.27 |
| | L | 39.84 ± 9.83 |
| Example 4 | H | 45.37 ± 10.94 |
| | M | 40.2 ± 9.82 |
| | L | 39.95 ± 10.03 |
| Example 5 | H | 43.84 ± 11.03 |
| | M | 41.54 ± 10.26 |
| | L | 40.19 ± 9.43 |
| Example 6 | H | 47.48 ± 11.48 |
| | M | 40.8 ± 10.72 |
| | L | 40.33 ± 9.76 |
| Comparative Example | H | 43.28 ± 9.45 |
| | M | 38.37 ± 11.58 |
| | L | 35.32 ± 7.39 |

TABLE 9-continued

Ox-LDL-C levels in serum of animals in each group

| Group | Mean Value ± Standard Deviation |
|---|---|
| Omega | 46.75 ± 11.54 |
| Atorvastatin Calcium | 45.44 ± 7.40 |

Comment: comparing the high-fat model group with the blank group, wherein ** indicates P < 0.01, and * indicates P < 0.05.

Figure 9:
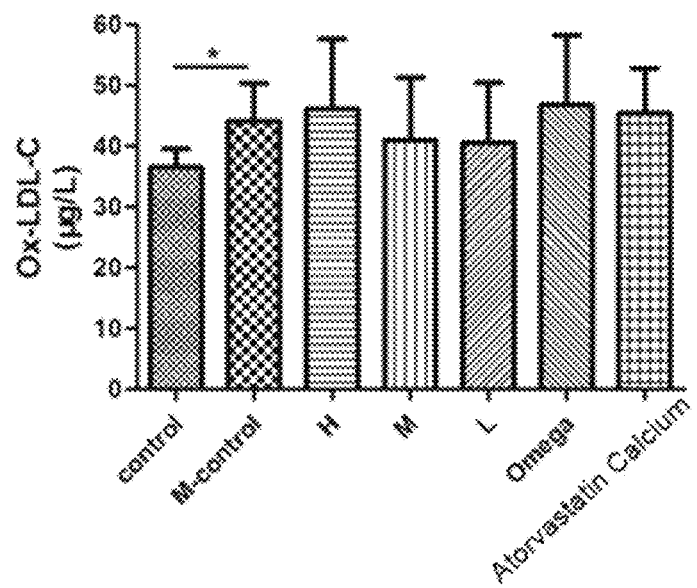
FIG. 9 shows influences of the composition provided by the present disclosure on ox-LDL content in the serum of SD rats; * indicates comparing the high-fat model group with the blank group, wherein ** indicates P<0.01; and * indicates P<0.05.

Results of Table 9 and FIG. 9 showed that ox-LDL-C contents in serum of the high, middle and low dosage groups of the composition and powder formulation provided by the present disclosure were respectively 46.12 μg/L, 40.95 μg/L and 40.53 μg/L. Comparing with the model control group (44.13 μg/L), there was no significant difference (P were respectively 0.720, 0.537 and 0.472, >0.05). Comparing each dosage group of the test sample with the Omega group and the atorvastatin calcium group, there was no significant difference. Results of the experiment showed that the composition and powder formulation provided by the present disclosure did not have an obvious effect on ox-LDL-C content in serum of SD rats.

Comparing the results of example 1~6 with that of the same dosage group of the comparative example, there was no significant difference (P>0.05).

(9) Effects of the Composition and Powder Formulation Provided by the Present Disclosure on Level of Lipoprotein A1 (Apo-A1) in Serum of SD Rats

TABLE 10

Apo-A1 levels in serum of animals in each group

| Group | | Mean Value ± Standard Deviation |
|---|---|---|
| M-control | | 2260.49 ± 201.25 |
| Control | | 2271.27 ± 237.59 |
| Example 1 | H | 2800.88 ± 546.97 |
| | M | 2621.04 ± 664.01 |
| | L | 2434.62 ± 476.26 |
| Example 2 | H | 2803.42 ± 537.38 |
| | M | 2629.08 ± 635.27 |
| | L | 2415.07 ± 435.72 |
| Example 3 | H | 2843.01 ± 533.84 |
| | M | 2643.95 ± 613.07 |
| | L | 2464.39 ± 454.32 |
| Example 4 | H | 2786.94 ± 549.34 |
| | M | 2604.73 ± 638.32 |
| | L | 2451.75 ± 499.03 |
| Example 5 | H | 2804.93 ± 523.15 |
| | M | 2674.62 ± 689.94 |
| | L | 2465.67 ± 515.32 |
| Example 6 | H | 2849.87 ± 639.03 |
| | M | 2674.48 ± 453.92 |
| | L | 2454.73 ± 531.75 |
| Comparative Example | H | 2839.74 ± 658.37 |
| | M | 2675.35 ± 493.08 |
| | L | 2505.77 ± 437.75 |
| Omega | | 2645.26 ± 626.25 |
| Atorvastatin Calcium | | 2693.75 ± 435.48 |

Figure 10:
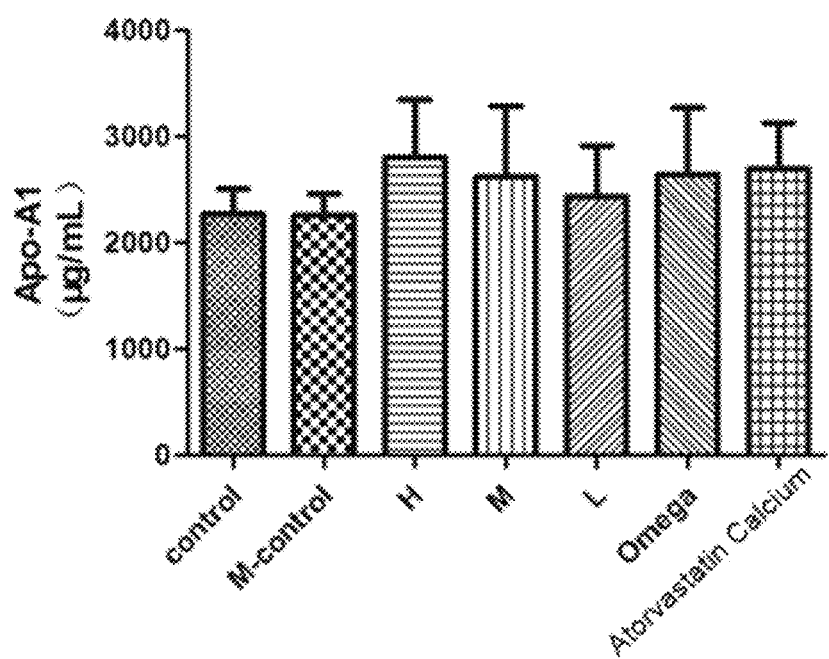
FIG. 10 shows influences of the composition provided by the present disclosure on apo-A1 content in the serum of SD rats.

Results of Table 10 and FIG. 10 showed that Apo-A1 contents in serum of the high, middle and low dosage groups of the composition and powder formulation provided by the present disclosure were respectively 2800.88 m/mL, 2621.04 μg/mL and 2434.62 m/mL. Comparing with the model control group (2260.49 m/mL), there was no significant difference (P were respectively 0.061, 0.251 and 0.438, >0.05). In addition, comparing each dosage group of the test sample with the Omega and atorvastatin calcium group, there was no significant difference (P were respectively 0.657, 0.949, 0.528 and 0.716, 0.828 and 0.349, >0.05). Results of the present experiment showed that composition and powder formulation provided by the present disclosure did not have an obvious effect of Apo-A1 content in serum of SD rats.

Comparing the results of example 1~6 with that of the same dosage group of the comparative example, there was no significant difference (P>0.05).

(10) Effects of the Composition and Powder Formulation Provided by the Present Disclosure on Level of Lipoprotein β (Apo-β) in Serum of SD Rats

TABLE 11

Apo-β levels in serum of animals in each group

| Group | | Mean Value ± Standard Deviation |
|---|---|---|
| M-control | | 1023.14 ± 101.20 |
| Control | | 882.53 ± 64.32* |
| Example 1 | H | 1123.71 ± 312.71 |
| | M | 1147.83 ± 262.00 |
| | L | 1178.31 ± 238.59 |
| Example 2 | H | 1120.47 ± 358.32 |
| | M | 1146.79 ± 213.64 |
| | L | 1173.52 ± 208.94 |
| Example 3 | H | 1120.27 ± 308.43 |
| | M | 1148.39 ± 253.13 |
| | L | 1184.35 ± 215.37 |
| Example 4 | H | 1125.73 ± 284.91 |
| | M | 1153.29 ± 254.65 |
| | L | 1184.93 ± 214.32 |
| Example 5 | H | 1120.48 ± 296.45 |
| | M | 1153.58 ± 253.14 |
| | L | 1185.93 ± 232.59 |
| Example 6 | H | 1124.75 ± 324.08 |
| | M | 1153.77 ± 232.42 |
| | L | 1183.64 ± 232.19 |
| Comparative Example | H | 1102.47 ± 431.73 |
| | M | 1153.35 ± 213.48 |
| | L | 1184.48 ± 342.87 |
| Omega | | 1000.08 ± 259.13 |
| Atorvastatin Calcium | | 735.00 ± 264.71# |

Comment: when comparing the high-fat model group with the blank group, wherein ** indicates P < 0.01, and * indicates P < 0.05; when comparing each experiment group with the high-fat model group, ## indicates P < 0.01, and # indicates P < 0.05.

Figure 11:
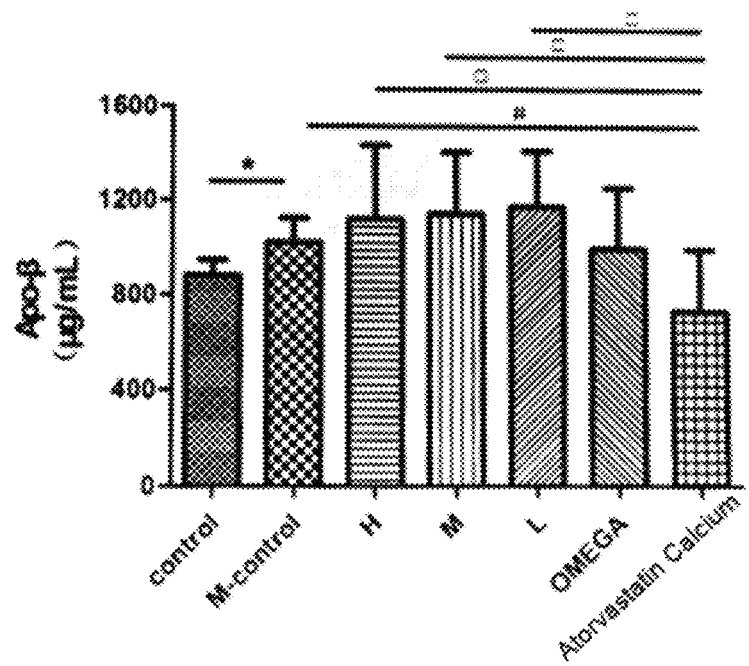
FIG. 11 shows influences of the composition provided by the present disclosure on apo-β content in the serum of SD rats; * indicates comparing the high-fat model group with the blank group, wherein ** indicates P<0.01; * indicates P<0.05; # indicates comparing each group with the high-fat model group, and ## indicates P<0.01; # indicates P<0.05; □ indicates comparing each dosage group with the atorvastatin calcium group, □ indicates P<0.01; and □□ indicates P<0.05.

Results of Table 11 and FIG. 11 showed that Apo-β contents in serum of the high, middle and low dosage groups of composition and powder formulation provided by the present disclosure were respectively 1123.71 μg/mL, 1147.83 μg/mL and 1178.31 μg/mL. It increased slightly comparing with the model control group (1023.14 μg/mL), but there was no significant statistical difference (P were respectively 0.482, 0.316 and 0.188, >0.05). Comparing the atorvastatin calcium control group with the model control group, Apo-β content in serum decreased (P=0.045, <0.05). Comparing each dosage group with the Omega control group, the Apo-β levels in serum of each group were not obviously different (P were respectively 0.474, 0.349 and 0.243, >0.05). Apo-β levels in serum of each dosage group were significantly lower than that of the atorvastatin calcium control group (P were respectively 0.043, 0.022 and 0.012, <0.05). Results of the present experiment showed that composition and powder formulation provided by the present disclosure did not have an obvious effect on Apo-β content in serum of SD rats.

Comparing the results of example 1~6 with that of the same dosage group of the comparative example, there was no significant difference (P>0.05).

The animal protocols in the present disclosure comply with the animal welfare principle. The experiment process is in line with the requirements of conditions of animal experiments. The data was detailed and accurate, and the results were reliable. After statistically analyzing, and evaluation standard referred to the *Technical specification for health care food inspection and evaluation* (2012 *Updated Edition*), the following conclusions were obtained:

(1) In the present experiment, comparing the model control group with the blank control group, triglyceride content in serum increased, contents of total cholesterol and low-density lipoprotein cholesterol in serum increased, and all the differences were significant, indicating that a SD rat model of the combined hyperlipidemia was established.

(2) Comparing each dosage group of the composition provided by the present disclosure with the model control group, triglyceride in serum of the high dosage group was lowered and the difference was significant; at the same time the total cholesterol in serum and the low-density lipoprotein cholesterol of each dosage group were not significantly higher than the model control group; and the high-density lipoprotein cholesterol in serum was significantly higher than model control group. Results of the present experiments indicated that high dosage group of composition provided by the present disclosure has a function of facilitating lowering triglyceride, and the results of animal experiment were positive.

(3) Results of the present study showed that the high dosage group of the composition provided by the present disclosure can significantly increase the content of the high-density lipoprotein cholesterol content in serum of SD rat, which functions by inhibiting the occurring of hyperlipidemia by increasing HDL-C content in serum.

The above descriptions are only preferred embodiments of the present disclosure. It should be noted that a number of modifications and refinements may be made by those skilled in the art without departing from the principles of the disclosure, and such modifications and refinements are also considered to be within the scope of the disclosure.

What is claimed is:

1. A method of lowering triglyceride, comprising administrating a composition comprising inulin, concentrated hawthorn juice, honeysuckle extract and concentrated peach juice to a subject in need thereof, wherein:
   solid content in the concentrated hawthorn juice is 40~70%, and solid content in the concentrated peach juice is 40~70%; and
   the mass ratio of inulin, the concentrated hawthorn juice, the honeysuckle extract and the concentrated peach juice is (1200~2400):(1200~2400):(50~200):(20~100).

2. The method according to claim 1, wherein the composition further comprises one selected from the group consisting of pectin, xylitol, stevioside, citric acid and mogroside, or a mixture thereof.

3. The method according to claim 1, wherein the composition further comprises pectin, xylitol, stevioside, citric acid and mogroside, and the mass ratio of inulin, the concentrated hawthorn juice, the honeysuckle extract, the concentrated peach juice, pectin, xylitol, stevioside, citric acid and mogroside is (1200~2400):(1200~2400):(50~200):(20~100):(30~50):(25~50):(10~50):(10~50):(5~15).

4. The method according to claim 3, wherein:
   the solid content in the concentrated hawthorn juice is 60%, and the solid content in the concentrated peach juice is 60%; and
   the mass ratio of inulin, the concentrated hawthorn juice, the honeysuckle extract, the concentrated peach juice, pectin, xylitol, stevioside, citric acid and mogroside is 1600:1800:110:40:45:35:30:15:6.

* * * * *